(12) United States Patent
Howell

(10) Patent No.: US 6,695,837 B2
(45) Date of Patent: Feb. 24, 2004

(54) POWER SUPPLY FOR IDENTIFICATION AND CONTROL OF ELECTRICAL SURGICAL TOOLS

(75) Inventor: Thomas A. Howell, Saratoga, CA (US)

(73) Assignee: Starion Instruments Corporation, Saratoga, CA (US)

( * ) Notice: Subject to any disclaimer, the term of this patent is extended or adjusted under 35 U.S.C. 154(b) by 0 days.

(21) Appl. No.: 10/099,500

(22) Filed: Mar. 13, 2002

(65) Prior Publication Data

US 2003/0176856 A1 Sep. 18, 2003

(51) Int. Cl.$^7$ ................................................ A61B 18/04
(52) U.S. Cl. ........................................................ 606/29
(58) Field of Search ............................. 606/1, 41, 34, 606/33, 32

(56) References Cited

U.S. PATENT DOCUMENTS

| | | | |
|---|---|---|---|
| 5,242,441 A | | 9/1993 | Avitall ........................ 606/41 |
| 5,383,874 A | * | 1/1995 | Jackson et al. ................. 606/1 |
| 5,593,406 A | | 1/1997 | Eggers et al. .................. 606/29 |
| 5,651,780 A | * | 7/1997 | Jackson et al. ................. 606/1 |
| 5,792,138 A | * | 8/1998 | Shipp ........................... 606/38 |
| 5,911,719 A | | 6/1999 | Eggers ......................... 606/31 |
| 6,017,354 A | * | 1/2000 | Culp et al. ................... 606/170 |
| 6,176,856 B1 | | 1/2001 | Jandak et al. ................. 606/29 |
| 6,235,020 B1 | * | 5/2001 | Cheng et al. .................. 606/34 |
| 6,235,027 B1 | | 5/2001 | Herzon ........................ 606/51 |

* cited by examiner

Primary Examiner—Michael Peffley
Assistant Examiner—Peter J Vrettakos
(74) Attorney, Agent, or Firm—K. David Crockett, Esq.; Crockett & Crockett

(57) ABSTRACT

An electronic circuit for identifying an electrical surgical tool and for providing a selectable constant current appropriate to the identified electrical surgical tool.

18 Claims, 5 Drawing Sheets

| Device | Rid | Vid | Output 40 | Output 41 | Output 42 |
|---|---|---|---|---|---|
| A | 1K Ohm | 4.5 | 1 | 1 | 1 |
| B | 10K Ohm | 2.5 | 0 | 1 | 1 |
| C | 51K Ohm | 0.83 | 0 | 0 | 1 |
| Foreign Device | Infinite | 0 | 0 | 0 | 0 |

POWER SUPPLY FOR IDENTIFICATION AND CONTROL OF ELECTRICAL SURGICAL TOOLS

FIELD OF THE INVENTIONS

The devices described below relate to power supplies intended to supply electrical power to medical instruments.

BACKGROUND OF THE INVENTIONS

Many electrical surgical devices are provided in the form of electrical surgical tools, such as a thermal cautery device, which can be plugged into a separate power supply. Typically, the power supplied to the electrical surgical tool must be carefully controlled; thus, the power supply includes circuitry to convert available AC power to AC, RF, or DC power at the desired output power levels or frequencies. For example, Herzon, Thermal Cautery Surgical Forceps, U.S. Pat. No. 6,235,027 (May 22, 2001), shows thermal cautery forceps using a power supply to deliver a regulated current to the resistive heating elements in the forceps. Our own cautery instruments, such as the Starion® Thermal Cautery Forceps, which comprise forceps with resistive heating elements disposed on the grasping tips, are designed to work with our PowerPack Surgical Power Supply. Currently marketed versions of this power supply provide a current to the resistive heating elements depending on the heat load and temperature of the resistive heating device. In addition to these two devices, many electrical surgical instruments are currently marketed to address a variety of surgical techniques and the number of surgical instruments available has been growing.

The increase in the variety of surgical instruments has introduced a problem in medical-grade power supplies. Most power supplies can operate with different kinds of medical instruments, as long as an electrical connection can be established between the power supply and the instrument. However, a medical device manufactured by one company may perform slightly differently than expected when the medical device is used in conjunction with a power supply from another company. Since many medical procedures require precise control of the electrical properties of the medical device, a surgeon or doctor may unintentionally harm a patient when the surgeon uses a power supply and a medical device from different manufacturers. For example, though the Starion® PowerPack provides optimal power to the various Starion® electrical surgical tools for which it is intended, the use of connectors available to other medical device manufacturers may permit use of non-Starion® electrical surgical tools with the PowerPack. When used in combination with such third party electrical surgical tools, it is not possible to ensure that the optimal amount of power is delivered to the tool. Thus, the tool may not function as desired, with the result that the patient may be harmed. Thus, a medical-grade power supply is needed which operates only with the instruments made by that manufacturer and tested with that model of power supply.

SUMMARY

The methods and devices described below relate to a power supply that identifies an electrical surgical tool, such as a thermal cautery device, and provides power only to electrical surgical tools that are identified by the power supply. The power supply uses a device identification circuit and a constant current circuit to control the power output to an electrical surgical tool. The device identification circuit identifies whether an electrical surgical tool is designed to be used with that power supply. If the device identification circuit recognizes the electrical surgical tool, then the constant current circuit will provide a constant current, or electrical power, to the tool. In addition, the constant current circuit will provide the tool with the amount of power required by that particular device. If the device identification circuit does not recognize the device connected to the power supply, then the constant current circuit provides no power to the device.

DETAILED DESCRIPTION OF THE INVENTIONS

Figure 1:
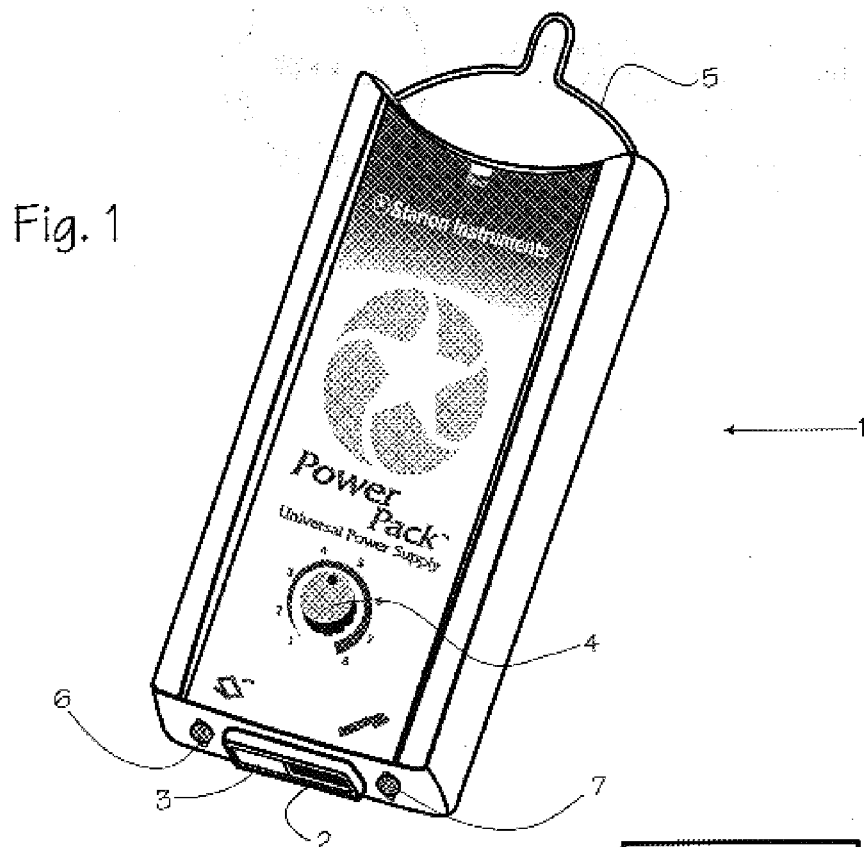
FIG. 1 illustrates the physical power supply box.

FIG. 1 illustrates a physical power supply box 1. The power supply box 1 is typically a non-sterile, reusable, AC powered device designed for use only with certain instruments, medical devices, electrosurgical devices, or other electrical surgical tools such as thermal cautery devices. The power supply is connected to an AC power source. The power supply has an on-off switch 2, an AC power connector 3, an LED power indicator 4, a control knob 5, and a hanger 6 suitable for suspending the power supply on a support object, such as an IV pole. The power supply is also equipped with an input 7 for an interface board, control board, or switches, and an output 8 to the medical instrument. The supply has input requirements of 100 to 240VAC at 50 to 60 Hz and at 80W, has a maximum output of 32VA, a no load voltage of 5V DC, and is operated at a duty cycle of about 5 seconds on and 10 seconds off. The output current is in the range of 2.4A to 4.4A, depending on which instrument is used and on the output desired by the user.

One version of the power supply, which is intended for use with cautery instruments, has three output heat levels: low, medium, and high. The levels correspond to the desired heat output of the thermal cautery instrument's resistive heating element or elements, and correspond to current outputs of the power supply. A tone indicates the level of heat being applied to the cautery device. For example, a low tone indicates a low heat setting, an interrupted low tone indicates a medium heat setting, and high tone indicates a high heat setting. Other devices have multiple heating elements and each element may have different heating levels. For medical devices with multiple settings or elements, the various settings and elements are adjustable. The adjustment of these settings or elements is typically facilitated by an interface board, or control board, that can switch between power levels or heating elements.

Figure 2:
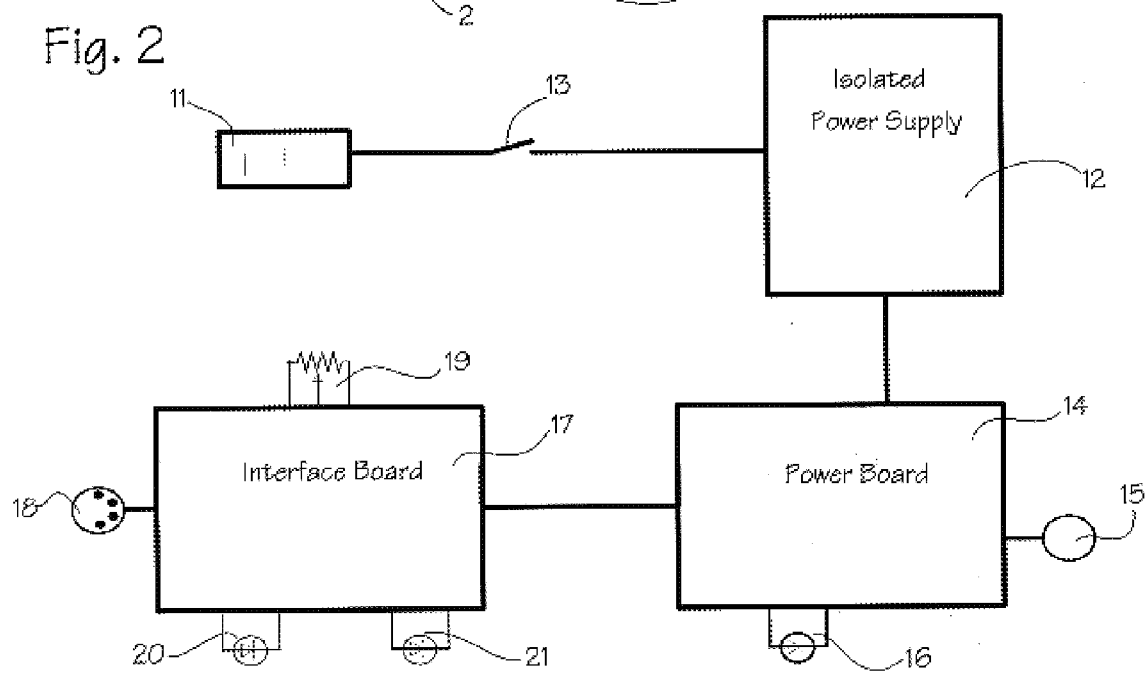
FIG. 2 is a block diagram of the power supply system.

FIG. 2 is a block diagram of the power supply system. Block 11 is the AC power input and is equipped with a power on/off switch 13. The AC power is connected to an isolated switching DC power supply 12, or AC to DC converter, through switch 13. However, the AC to DC converter can be replaced with an AC to low frequency AC converter, an AC to high frequency AC converter, or an AC to low power AC converter. The isolated switching DC power supply 12 typically has an output of +5 volts DC. In addition, the isolated switching DC power supply is UL rated for heart contact, meaning that the output of the power supply can directly touch the patient. The DC power supply 12 is connected to a power board 14 which contains a constant current circuit. The power board 14 is also connected to the electrical surgical tool 15, a power LED 16 indicating whether the power supply is "on", and an interface or control board 17. The interface board contains a device identification circuit and a control voltage circuit. The interface board 17 is optionally connected to a switch module 18, which typically has pedal or push button switches. The output of the switch module allows the user to select the level of power desired for a given procedure, or to select other modes of operation available to particular medical devices, when the switch module is connected to the control voltage means described below. Alternatively, the switches can directly control the power level provided to the medical device. The interface board 17 is also attached to a current control knob or switch 19, a device LED 20 indicating whether an attached device is capable of functioning with the power supply, and a switch LED 21 that indicates that use of the switch module 18 is required. Note that other interface boards may be added to the power board.

Figure 3:
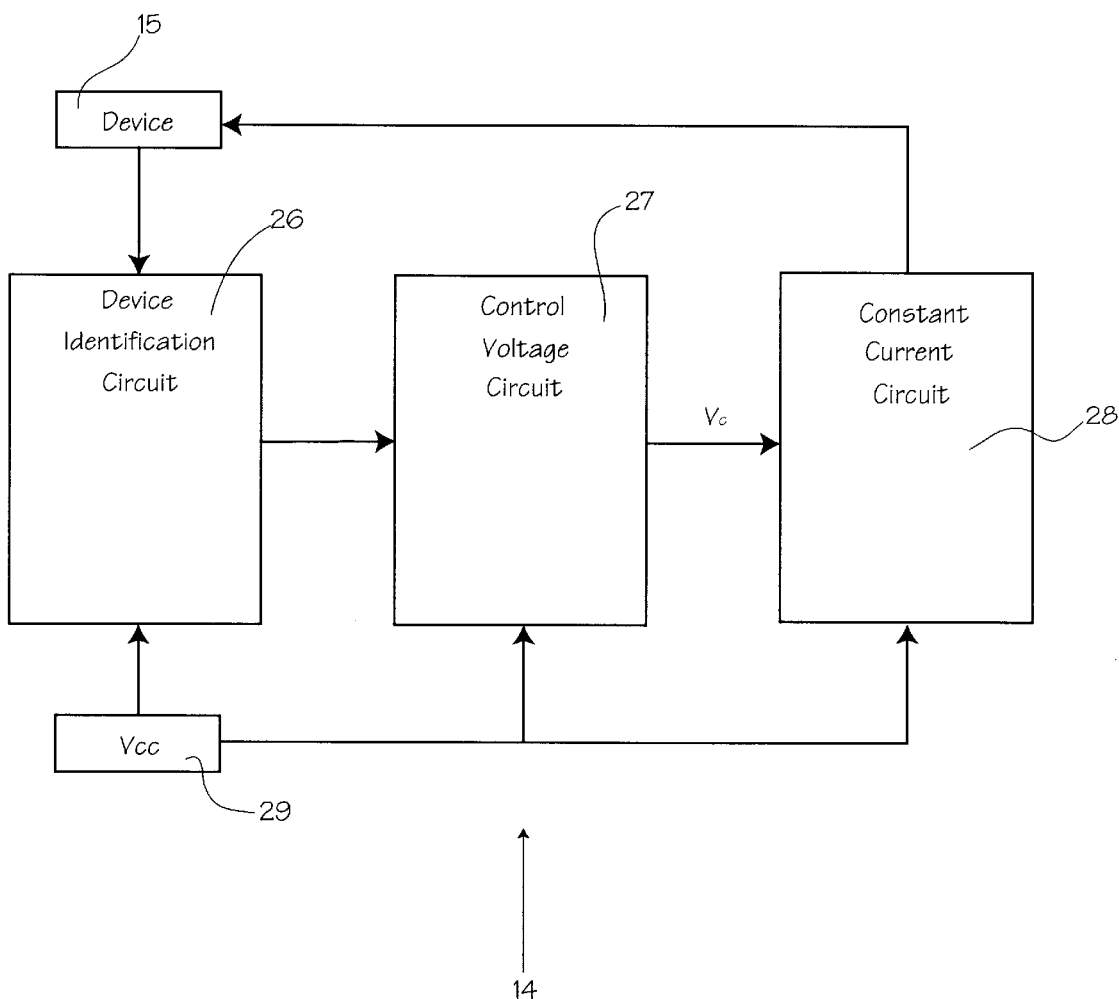
FIG. 3 is a block diagram of the power board system.

FIG. 3 is a block diagram of the power board system. The power board 14 is conceptualized as three circuits: a device identification circuit 26, a control voltage circuit 27, and a constant current circuit 28. The electrical surgical device 15 is electrically connected to the device identification circuit 26 and receives current from the constant current circuit 28. A constant DC power source, $V_{cc}$ (item 29), is provided to all three circuits 27, 28, and 29, and is operated to supply power at about +5 volts DC. Note that other circuit blocks may be added, such as a circuit that provides a tone indicating the level of power running through the medical device or a circuit that facilitates the use of additional switches or pedals to control the power output of the power supply.

Figures 4, 5:
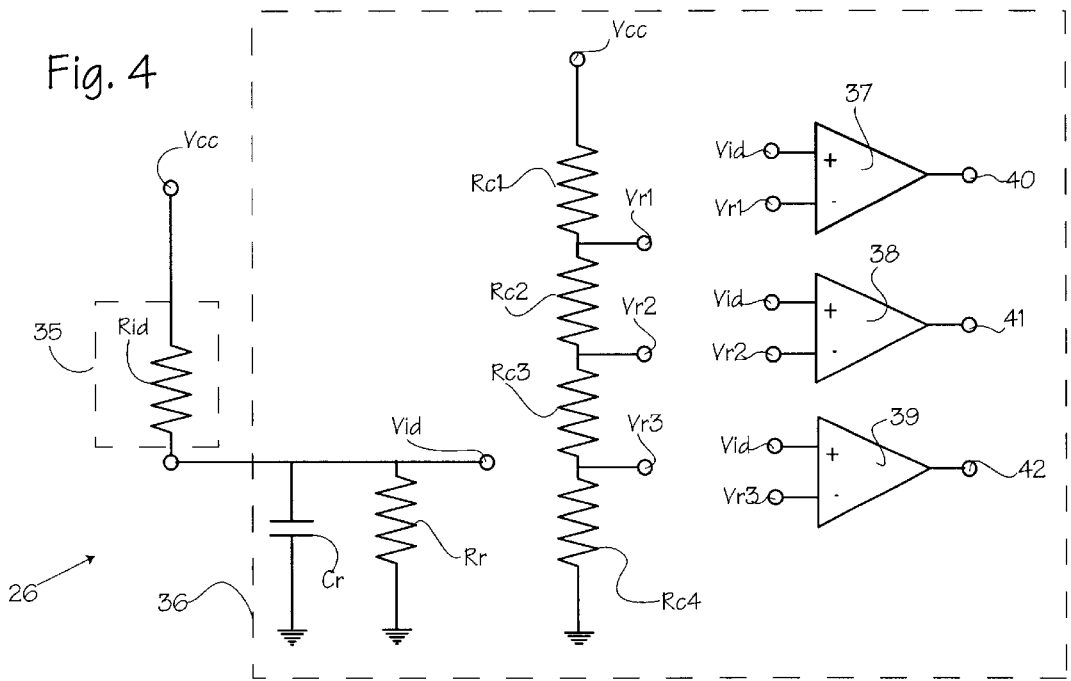
FIG. 4 is a circuit diagram of the device identification circuit.
FIG. 5 is a device identification table showing specific values of the identification resistor, the identification voltage, and the comparator outputs for three distinct thermal cautery devices and a foreign device.

FIG. 4 is a circuit diagram of the device identification circuit 26, which includes all three diagrams shown in FIG. 4. The portion of the device identification circuit shown in area 35 (comprising the box 35 shown in phantom) contains the portion of the identification circuit located in the electrical surgical tool. The portion of the ID circuit shown in area 36 (comprising the box 36 shown in phantom) is located in the power supply box. Nevertheless, the various components of the device identification circuit can be placed in either the electrical surgical device or the power supply box. For example, all of the circuit could be inside the electrical surgical tool or all of the circuit could be placed inside the power supply box. However, if the identification resistor, $R_{id}$, is placed inside the power supply box, then means are provided such that a specific electrical surgical device plugs into a corresponding identification resistor. For example, a different outlet in the power supply box can be provided for each electrical surgical device. Alternatively, each electrical surgical device plug can have a different pin arrangement that plugs into a single outlet in the power supply box. In this case, the pin arrangement selects the proper identification resistor.

The device identification circuit can determine whether an electrical surgical device is plugged in or plugged in properly, whether the device is a device for which the power supply is designed, and which of a plurality of electrical surgical devices designed for use with the power supply is electrically connected to the power supply. In addition, the circuit of FIG. 4 constitutes a device identification means (or an electrical surgical device identification means or a thermal cautery device identification means), though the circuit may be varied in many respects. For example, the circuit of FIG. 4 is designed to identify three medical devices, though the circuit could add additional resistors to the resistor ladder and add additional comparators so that the device identification circuit can identify a plurality of electrical surgical devices or other kinds of electrical medical devices. In addition, capacitors can be added or subtracted from the circuit in order to create different kinds of filters. Also, the resistive heating element of the electrical surgical device can comprise the identification resistor as long as the resistive heating element of each electrical surgical device has a distinct resistance.

Referring again to FIG. 4, a voltage $V_{cc}$ is placed across a resistor, $R_{id}$, which is located in the plug of the medical device, and a reference resistor, $R_r$, connects to ground. An identifying voltage, $V_{id}$, develops across $R_r$. Note that $V_{id}$ varies with the value of $R_{id}$. $R_{id}$ is set by the manufacturer and is unique to a particular model of medical device. A capacitor, $C_r$, is placed in parallel with the reference resistor and operates as a low pass filter.

The identifying voltage, $V_{id}$, is sent to a comparator, which compares $V_{id}$ to a reference voltage, $V_r$. If the identifying voltage, $V_{id}$, is greater than the reference voltage, $V_r$, then the comparator (which can be a true comparator or an operational amplifier operated as a comparator) outputs a "1" signal. If the identifying voltage is less than the reference voltage, then the comparator outputs a "0" signal. The output of the comparator is provided to the control voltage circuit 27, which generates a control voltage, $V_c$. The control voltage determines, through the constant current circuit 28, the amount of power provided to the medical device.

The device identification circuit in FIG. 4 is designed to detect three kinds of medical instruments, each of which has a separate identifying resistor, $R_{id}$. Thus, the voltage cascade circuit has four comparison resistors, $R_{c1}$, $R_{c2}$, $R_{c3}$, and $R_{c4}$, placed in a resistor ladder. The resistor ladder produces a voltage cascade comprising a series of reference voltages. A reference voltage is taken between each of the reference resistors, the reference voltages comprising $V_{r1}$, $V_{r2}$, and $V_{r3}$. Each reference voltage is provided to the negative terminal of a distinct comparator; thus, $V_{r1}$ is provided to comparator 37, $V_{r2}$ is provided to comparator 38, and $V_{r3}$ is provided to comparator 39. On the other hand, the same identifying voltage, $V_{id}$, is provided to the positive terminal of each comparator. The output of each comparator, 40, 41, and 42, is provided to the control voltage circuit 27.

A first model of a medical instrument (device A) has an identifying resistor, $R_{id}$, with the smallest value. In this case the identifying voltage, $V_{id}$, will be higher than all three of the reference voltages. Thus, all three comparators will output a "1" signal. The fact that all three comparators output a signal is communicated through the control voltage circuit 27, which outputs a control voltage, $V_c$. The constant current circuit 28 then uses the control voltage to control electrical power to device A in an amount appropriate to device A.

Similarly, a second model of medical instrument (device B) will have an identifying resistor, $R_{id}$, of medium resistance. In this case the identifying voltage, $V_{id}$, will be lower than the first reference voltage, $V_{r1}$, but higher than the other two, $V_{r2}$ and $V_{r3}$. Thus, only comparators 38 and 39 will produce a "1" output. Accordingly, the constant current circuit 28 will recognize that device B is connected to the power supply. On the other hand, if a third model of medical instrument (device C) is connected to the power supply then $V_{id}$ will be less than $V_{r2}$ and $V_{r2}$, but greater than $V_{r3}$. In this case, only comparator 39 will report a "1" output and the constant current circuit 28 will recognize that device C is connected to the power supply. However, if $R_{id}$ is not present or does not have the correct value, then all of the comparators will output a "0" signal. In this case the control voltage will be "0" and then the constant current circuit will provide no power to the device. Thus, the power supply using the device identification circuit of FIG. 4 will only work with thermal cautery devices A, B, and C.

The various values of $C_r$, $R_r$, $R_{id}$, $R_c$, $V_r$, and $V_{id}$ are set by the manufacturer and can have a wide range of values. In one embodiment $V_{cc}$=+5V, $C_r$=10 μF, $R_r$=10 KΩ, $R_{c1}$=15 KΩ, $R_{c2}$=20 KΩ, $R_{r3}$=10 KΩ, and $R_{c4}$=5.1 KΩ. In this case $V_{r1}$=3.5V, $V_{r2}$=1.5V, and $V_{r3}$=0.5V. In addition, there are three thermal cautery devices designed by the manufacturer to operate with the power supply, the thermal cautery devices having a $R_{id}$ values of 1 KΩ, 10 KΩ, and 51 KΩ respectively. Furthermore, $V_{id}$ will have 3 different values, one for each thermal cautery device, as shown in the table of FIG. 5.

FIG. 5 is a device identification table showing the specific values of the identification resistor, the identification voltage, and the comparator outputs for the three distinct thermal cautery devices and a foreign device. The columns in FIG. 5 reflecting comparator outputs 40, 41, and 42 show that each thermal cautery device has a unique set of comparator outputs. In the comparator output columns of FIG. 5, a "1" indicates an output signal of "1" and a "0" indicates an output signal of "0". Note that for each device (table row) $V_{r1}$=3.5V, $V_{r2}$=1.5V, and $V_{r3}$=0.5V The table of FIG. 5 shows that when thermal cautery device A, with an $R_{id}$ of 1 KΩ, is plugged into the power supply then $V_{id}$ is 4.5V, which is higher than all three of the reference voltages, $V_{r1}$ (3.5V), $V_{r2}$ (1.5V), and $V_{r3}$ (0.5V). Thus, comparators 37, 38, and 39 all output a "1" signal and the system then knows that thermal cautery device A is plugged into the power supply. Applying similar logic, the system can tell if thermal cautery devices B or C are plugged into the system. However, if a foreign device is plugged into the system, or if no device is plugged into the system, then $R_{id}$ is infinity and thus $V_{id}$=0. If $V_{id}$ is 0 then $V_{id}$ is less than all three values of $V_r$; accordingly, all of the comparators will output a "0" signal and the constant current circuit 28 will provide no electrical power to the thermal cautery device.

The output of the device identification circuit, 40, 41, and 42, is fed into the input of the control voltage circuit 27. The control voltage circuit is a series of logic gates and analog circuits connected to the comparators and, optionally, to switches in the interface board. The logic gates, analog circuits, and switches constitute a control voltage means. The control voltage circuit 27 outputs a control voltage, $V_c$, based on the output of the comparators and, optionally, based on the interface board switches 18. The control voltage that is output by the control voltage means is unique to a particular electrical surgical device that has been designed to work with the power supply. The switches and the control voltage circuit allow the user to select a control voltage from a set number of control voltages. The constant current circuit 28 uses the control voltage, $V_c$, to determine the amount of current delivered to the thermal cautery device.

Figure 6:
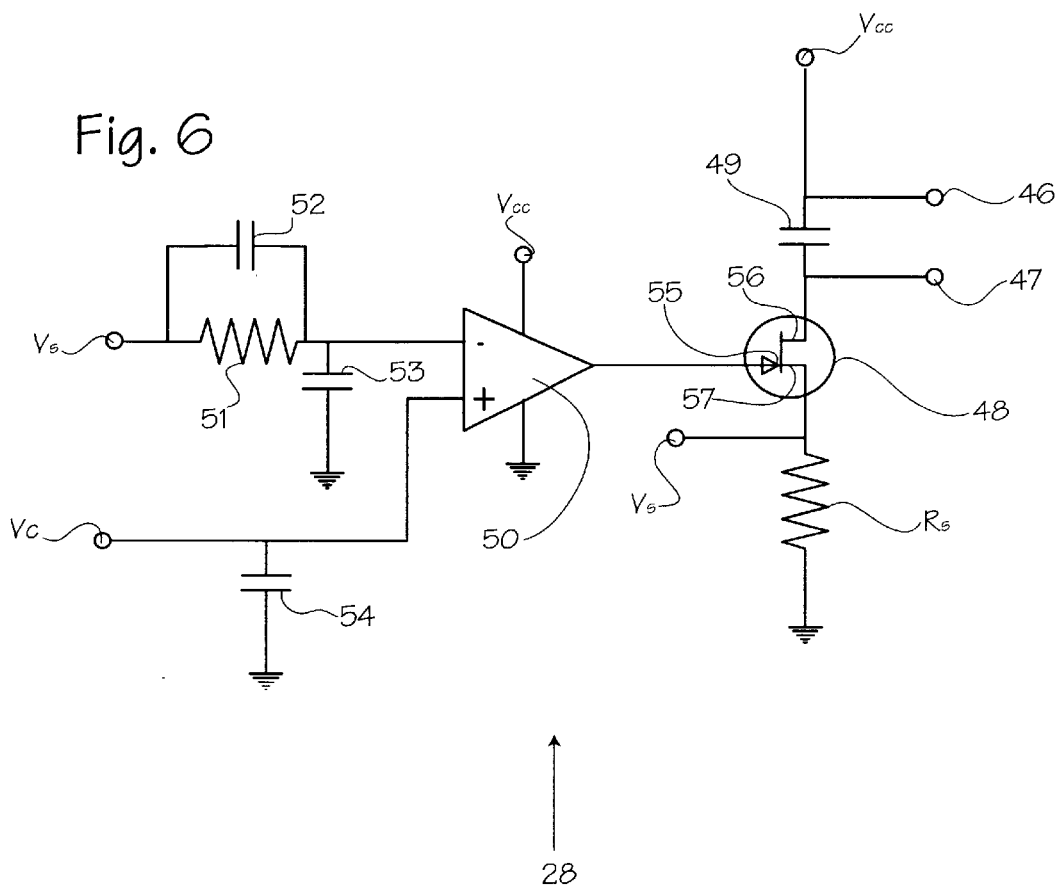
FIG. 6 is a circuit diagram of the constant current circuit.

FIG. 6 is a circuit diagram of the constant current circuit 28. The main current path proceeds from $V_{cc}$ (typically +5 volts), through output plug (between terminals 46 and 47 when the terminals are electrically connected), through a power MOSFET 48 and finally through a sense resistor, $R_s$, used to sense the amount of current, $I_{main}$, flowing through the main current path. Other kinds of transistors can also be used, such as a JFET transistor or an NPN transistor (BJT transistor). A capacitor, 49, is placed between the terminals of the output plug and acts as a low pass filter. When current flows through the main current path, $R_s$ generates a sense voltage, $V_s$, proportional to the main current ($V_s$=$I_{main}$×$R_s$). The circuit provides the sense voltage, $V_s$, to the negative terminal of an operational amplifier 50 through a low pass filter comprising resistor 51 and capacitors 52 and 53. The operational amplifier 50 is also connected to ground and to $V_{cc}$. The positive terminal of the operational amplifier is connected to the control voltage, $V_c$, through a low pass filter comprising capacitor 54. The operational amplifier compares the control voltage, $V_c$, to the sense voltage, $V_s$, and generates an output that controls the gate 55 of the power MOSFET 48. (The MOSFET drain 56 and source 57 are shown for convenience). The result is that the operational amplifier 50 adjusts the current flowing through the power MOSFET 48 until the sense voltage is equal to the control voltage ($V_s$=$V_c$) Thus, the constant current circuit 28 maintains the current at a steady level. The amount of current is set by the value of the sense resistor, $R_s$. For example, if the sense resistor, $R_s$=0.1Ω and the control voltage, $V_c$=0.1V, then the main current, $I_{main}$=1.0A.

The output plug (terminals 46 and 47) is electrically connected to the medical instrument's resistive heating elements, thus completing the electrical circuit. Accordingly, the current flowing through the main current path powers the medical instrument reliably and selectably. The circuit of FIG. 6 constitutes a constant current means, though the circuit can be varied in many respects. For example, the capacitors and resistors can take on different values, may be taken out of the circuit, or other capacitors and resistors may be added to accomplish different filtering effects. In addition, the circuit can be similarly modified to provide different output currents for a given control voltage.

Figure 7:
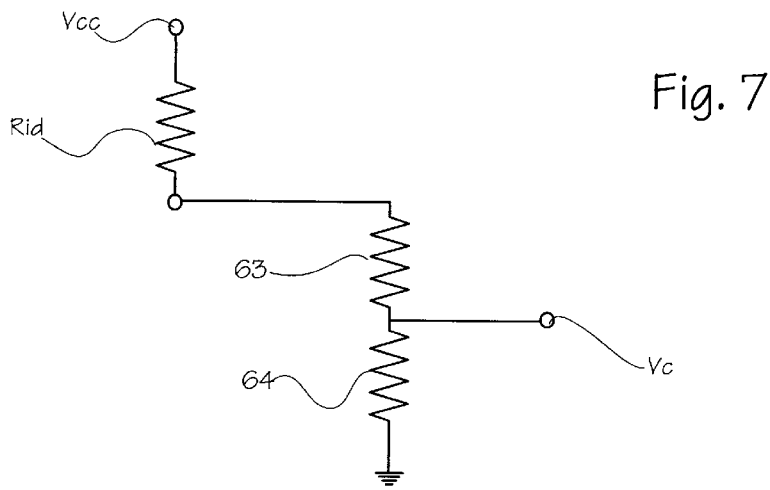
FIG. 7 is a circuit diagram of an alternate device identification circuit.

FIG. 7 is a circuit diagram of an alternate device identification circuit. A voltage, $V_{CC}$, is placed across a resistor, $R_{id}$, which is located in the plug of the electrical surgical tool. $R_{id}$ is set by the manufacturer and is unique to a particular thermal cautery device. A second resistor, 63, is connected to a control resistor, 64, which itself connects to ground. A control voltage, $V_c$, develops across control resistor 64 and $V_c$ varies with the value of $R_{id}$. The control voltage is provided to a constant current circuit, such as that shown in FIG. 5, which provides a constant current to the thermal cautery device. The output current is a function of $V_c$ and $R_{id}$ ($I_{output}$=$V_c$/$R_{id}$)

Figure 8:
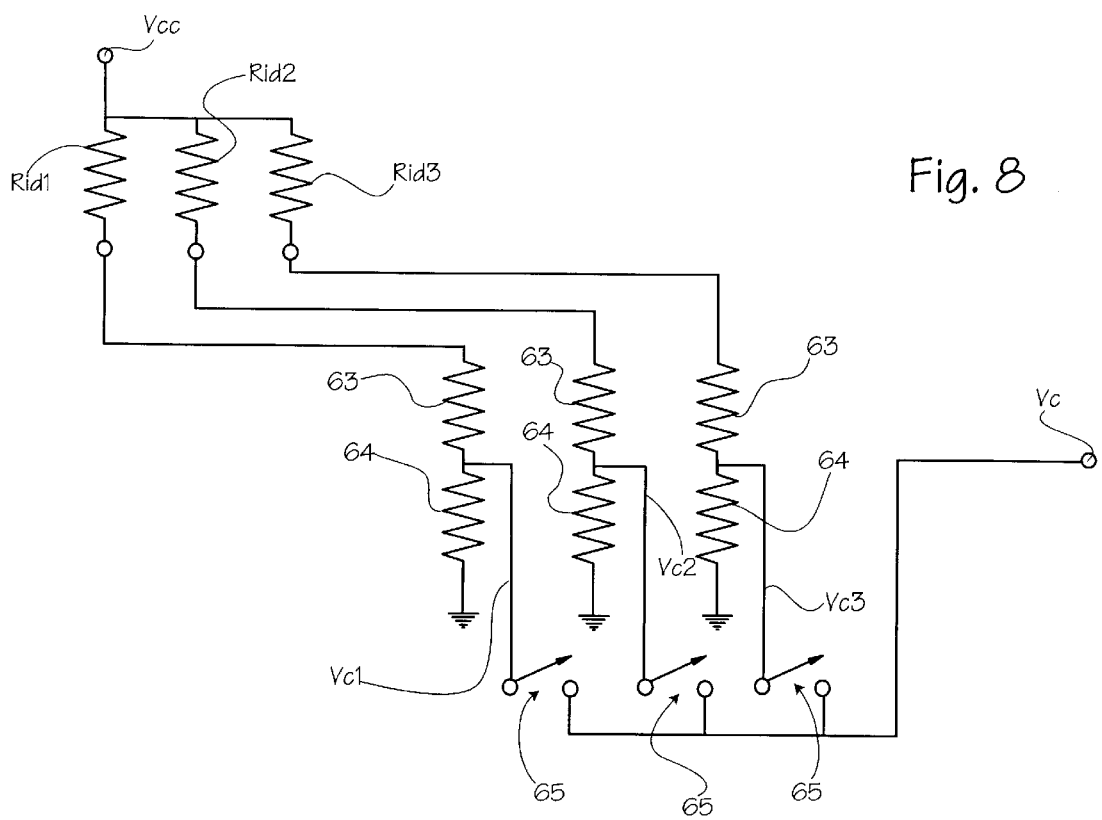
FIG. 8 is a circuit diagram of an alternate device identification circuit with switching.

FIG. 8 is a circuit diagram of an alternate device identification circuit with switching. Three circuits, similar to the one in FIG. 7, are combined using three different identification resistors, $R_{id1}$, $R_{id2}$, and $R_{id3}$, though resistors 63 and 64 have the same value in all three circuits. In addition, a switch 65 is provided in each individual circuit between the second resistor 63 and the control resistor 64. The switch 65 can be any kind of switch, such as a push button, a pedal, or a knob. Selecting a switch chooses one of the control voltages, $V_{c1}$, $V_{c2}$, or $V_{c3}$, and sends that control voltage to a constant current circuit, such as the one shown in FIG. 6. The constant current circuit then provides a constant current to the electrical surgical tool appropriate to the particular thermal cautery device and appropriate to the switch or switch combination selected. In one embodiment the values of the components are $R_{id1}=2.75$ K$\Omega$, $R_{id2}=3.67$ K$\Omega$, $R_{id3}=5.5$ K$\Omega$, $R_{63}=10$ K$\Omega$, $R_{64}=1$ K$\Omega$. Since V=IR then in this embodiment $I_{output}=11$ K$\Omega/R_{id}$.

Depending on the design of the constant current circuit, control voltage circuit, or other additional circuit, the combination of switches can control a variety of variables. For example, an electrical surgical tool may have one subcomponent that requires power. In this case the three switches control whether the device receives a "high", "medium", or "low" amount of power. The constant current circuit shown in FIG. 6 can operate with the device identification circuit of FIG. 8 to perform this function.

Alternatively, other control voltage circuits can add additional capabilities when used in conjunction with the switch design of FIG. 8. For example, an electrical surgical tool can have three subcomponents, each of which require power. The three switches determine which, if any, of the subcomponents receive power. For other constant current circuits it is possible to use different combinations of open and closed switches. For the circuit shown in FIG. 8 there are eight possible switch combinations. Each combination of switch positions generates a distinct control voltage that can control different elements or power levels of the electrical surgical tool.

A plurality of switch circuits is also possible. In the case of a electrical surgical tool with three powered subcomponents, each of which having three power settings, then nine switches can control which subcomponent receives a given amount of power (depending on the design of the constant current circuit and control voltage circuits). In addition, a plurality of electrical surgical tool can be attached to the circuit, each electrical surgical tool having a unique identifying resistor. In this case the plurality of switches determine which, if any, of the devices are "on". Finally, a plurality of switches can be provided on a circuit that accommodates multiple devices, each device having multiple powered subcomponents, each powered subcomponent having multiple power levels, and wherein different combinations of switch positions control different aspects of the device.

Although the methods, devices, and circuits are described in relation to electrical surgical tools, the same methods, devices, and circuits can be used with other kinds electrical devices where device identification is desired. For example, electrical surgical tools using DC, AC, or RF power can use the. device identification methods described above. Electrical surgical tools useable with the device identification circuit also include ablation devices, thermal ligation devices, thermal cautery devices, electrocautery devices and other kinds electro-medical instruments. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A system for performing thermal cautery comprising:
   at least one group of thermal cautery devices, wherein each group of thermal cautery devices comprises a plurality of thermal cautery devices, wherein each of the thermal cautery devices in each group comprises a resistive heating element;
   a power supply capable of providing power to any particular thermal cautery device in each group, wherein the power supply further comprises a means for identifying a thermal cautery device, said means for identifying a thermal cautery device capable of identifying the group to which a particular thermal cautery device belongs when the particular device is electrically connected to the power supply, and wherein each of the thermal cautery devices is designed to operate with the power supply;
   wherein each thermal cautery device comprises an identification resistor electrically connected thereto, wherein the identification resistors within a particular group of devices have the same resistance, and wherein the identification resistors of the devices of one group have a distinct resistance from the identification resistors of the devices of all other groups;
   wherein the means for identifying a thermal cautery device comprises:
   a reference resistor placed in series with the identification resistor when the identification resistor is electrically connected to the power supply, said reference resistor also electrically connected to ground such that an identifying voltage develops across the reference resistor when power is applied to the system;
   a resistor ladder comprising a plurality of comparison resistors electrically connected to each other in a resistor ladder, said resistor ladder electrically connected to the power supply and to ground, wherein a corresponding plurality of reference voltages develops across the resistor ladder when power is applied to the system;
   a plurality of comparators, wherein the positive terminal of each of the plurality of comparators is electrically connected to the identifying voltage, wherein the negative terminal of a particular comparator is electrically connected to a particular reference voltage, and wherein each of the reference voltages is applied to the negative terminal of a corresponding comparator;
   wherein each particular comparator produces an output signal if the voltage at the positive terminal of the particular comparator is higher than the voltage at the negative terminal of the particular comparator; and
   wherein a combination of all comparator outputs uniquely identifies the group to which a particular thermal cautery device belongs when the particular thermal cautery device is electrically connected to the system and power is applied to the system.

2. The system of claim 1 wherein the at least one group of thermal cautery devices comprises a first group of thermal cautery devices, a second group of thermal cautery devices and a third group of thermal cautery devices, and wherein the identification resistors of the first group of thermal cautery devices have a resistance value of about 1 K$\Omega$, the identification resistors of the second group of thermal cautery devices have a resistance value of about 10 K$\Omega$ and wherein the identification resistors of the third group of thermal cautery devices have a resistance value of about 51 K$\Omega$.

3. The system of claim 1 further comprising a capacitor electrically connected in parallel with the reference resistor.

4. The system of claim 1 wherein the power supply further comprises:

a power MOSFET, wherein the resistive heating element of a particular thermal cautery device is electrically connected to the drain of the power MOSFET when the particular thermal cautery device is electrically connected to the power supply;

a sense resistor electrically connected to ground and to the source of the power MOSFET, wherein a sense voltage develops across the sense resistor when power is applied to the system;

an operational amplifier, wherein the output of the operational amplifier is electrically connected to the gate of the power MOSFET, wherein the negative terminal of the operational amplifier is electrically connected to the sense voltage, and wherein the positive terminal of the operational amplifier is electrically connected to a control voltage, whereby a current in the resistive heating element will be adjusted until the sense voltage equals the control voltage;

wherein the control voltage is based on a combination of the outputs of the plurality of comparators.

5. The system of claim 4 wherein the power supply provides power to a particular thermal cautery device only if the particular thermal cautery device belongs to one of the groups of thermal cautery devices.

6. The system of claim 1 wherein the at least one group of thermal cautery devices comprises three groups of thermal cautery devices, wherein the resistor ladder comprises four resistors having distinct resistances, and wherein the plurality of comparators comprises three comparators.

7. The system of claim 1 further comprising a means for indicating to an operator whether the particular thermal cautery device is capable of functioning with the power supply.

8. The system of claim 1 wherein the power supply provides power to a particular thermal cautery device electrically connected to the power supply based on the group to which the particular thermal cautery device belongs.

9. The system of claim 1 wherein the power supply provides power to a particular thermal cautery device only if the particular thermal cautery device belongs to one of the groups of thermal cautery devices.

10. A system for performing thermal cautery comprising:
at least one group of thermal cautery devices, wherein each group of thermal cautery devices comprises a plurality of thermal cautery devices, wherein each of the thermal cautery devices in each group comprises a resistive heating element;

a power supply capable of providing power to any particular thermal cautery device in each group, wherein the power supply further comprises a means for identifying a thermal cautery device, said means for identifying a thermal cautery device being capable of identifying the group to which a particular thermal cautery device belongs when the particular device is electrically connected to the power supply, and wherein the means for identifying a thermal cautery device is further capable of determining whether a thermal cautery device electrically connected to the power supply is designed to operate with the power supply;

wherein each thermal cautery device comprises an identification resistor electrically connected thereto, wherein the identification resistors within a particular group of devices have the same resistance, and wherein the identification resistors of the devices of one group have a distinct resistance from the identification resistors of the devices of all other groups;

wherein the means for identifying a thermal cautery device comprises:
a reference resistor placed in series with the identification resistor when the identification resistor is electrically connected to the power supply, said reference resistor also electrically connected to ground such that an identifying voltage develops across the reference resistor when power is applied to the system;

a resistor ladder comprising a plurality of comparison resistors electrically connected to each other in a resistor ladder, said resistor ladder electrically connected to the power supply and to ground, wherein a corresponding plurality of reference voltages develops across the resistor ladder when power is applied to the system;

a plurality of comparators, wherein the positive terminal of each of the plurality of comparators is electrically connected to the identifying voltage, wherein the negative terminal of a particular comparator is electrically connected to a particular reference voltage, and wherein each of the reference voltages is applied to the negative terminal of a corresponding comparator;

wherein each particular comparator produces an output signal if the voltage at the positive terminal of the particular comparator is higher than the voltage at the negative terminal of the particular comparator;

wherein a combination of all comparator outputs uniquely identifies the group to which a particular thermal cautery device belongs when the particular thermal cautery device is electrically connected to the system and power is applied to the system; and wherein a combination of all comparator outputs also identifies whether a thermal cautery device electrically connected to the system is designed to operate with the power supply.

11. The system of claim 10 wherein the at least one group of thermal cautery devices comprises a first group of thermal cautery devices, a second group of thermal cautery devices and a third group of thermal cautery devices, and wherein the identification resistors of the first group of thermal cautery devices have a resistance value of about 1 K$\Omega$, the identification resistors of the second group of thermal cautery devices have a resistance value of about 10 K$\Omega$ and wherein the identification resistors of the third group of thermal cautery devices have a resistance value of about 51 K$\Omega$.

12. The system of claim 10 further comprising a capacitor electrically connected in parallel with the reference resistor.

13. The system of claim 10 wherein the power supply further comprises:
a power MOSFET, wherein the resistive heating element of a particular thermal cautery device is electrically connected to the drain of the power MOSFET when the particular thermal cautery device is electrically connected to the power supply;

a sense resistor electrically connected to ground and to the source of the power MOSFET, wherein a sense voltage develops across the sense resistor when power is applied to the system;

an operational amplifier, wherein the output of the operational amplifier is electrically connected to the gate of the power MOSFET, wherein the negative terminal of the operational amplifier is electrically connected to the sense voltage, and wherein the positive terminal of the operational amplifier is electrically connected to a control voltage, whereby a current in the resistive heating element will be adjusted until the sense voltage equals the control voltage;

wherein the control voltage is based on a combination of the outputs of the plurality of comparators.

14. The system of claim 13 wherein the power supply provides power to a particular thermal cautery device only if the particular thermal cautery device belongs to one of the groups of thermal cautery devices.

15. The system of claim 10 wherein the power supply provides power to a particular thermal cautery device electrically connected to the power supply based on the group to which the particular thermal cautery device belongs.

16. The system of claim 10 wherein the power supply provides power to a particular thermal cautery device only if the particular thermal cautery device belongs to one of the groups of thermal cautery devices.

17. The system of claim 10 wherein the at least one group of thermal cautery devices comprises three groups of thermal cautery devices, wherein the resistor ladder comprises four resistors having distinct resistances, and wherein the plurality of comparators comprises three comparators.

18. The system of claim 10 further comprising a means for indicating to an operator whether the particular thermal cautery device is capable of functioning with the power supply.

* * * * *